United States Patent
Klaassen

(10) Patent No.: US 10,426,939 B2
(45) Date of Patent: Oct. 1, 2019

(54) DISPOSABLE LIQUID APPLICATOR SACHET

(71) Applicant: DAKLAPACK EUROPE B.V., Lelystad (NL)

(72) Inventor: Dave Willem Klaassen, Ermelo (NL)

(73) Assignee: DAKLAPACK EUROPE B.V., Lelystad (NL)

( * ) Notice: Subject to any disclaimer, the term of this patent is extended or adjusted under 35 U.S.C. 154(b) by 325 days.

(21) Appl. No.: 15/308,259

(22) PCT Filed: Apr. 30, 2015

(86) PCT No.: PCT/NL2015/050295
§ 371 (c)(1),
(2) Date: Nov. 1, 2016

(87) PCT Pub. No.: WO2015/167336
PCT Pub. Date: Nov. 5, 2015

(65) Prior Publication Data
US 2017/0065802 A1 Mar. 9, 2017

(30) Foreign Application Priority Data
May 2, 2014 (NL) .................................... 2012741

(51) Int. Cl.
*A61F 13/40* (2006.01)
*B65D 75/58* (2006.01)
*A61M 35/00* (2006.01)

(52) U.S. Cl.
CPC ........ *A61M 35/006* (2013.01); *A61M 35/003* (2013.01); *B65D 75/5866* (2013.01); *A61M 35/00* (2013.01); *A61M 2207/00* (2013.01)

(58) Field of Classification Search
CPC .. A61M 35/00; A61M 35/003; A61M 35/006; A61M 2207/00; B65D 75/5866
See application file for complete search history.

(56) References Cited

U.S. PATENT DOCUMENTS 3,917,116 A * 11/1975 Mason .................... A45D 37/00
206/484
8,104,986 B2 * 1/2012 Nash .................... A61M 35/003
401/123

(Continued)

FOREIGN PATENT DOCUMENTS

| EP | 0 294 189 A2 | 12/1988 |
| GB | 2 339 185 A | 1/2000 |

*Primary Examiner* — Tatyana Zalukaeva
*Assistant Examiner* — Gabriella E Burnette
(74) *Attorney, Agent, or Firm* — Birch, Stewart, Kolasch & Birch, LLP

(57) ABSTRACT

The invention relates to a liquid applicator sachet comprising a top sheet sealed onto a base sheet such that the sheets define between them, in a reservoir portion, a reservoir for holding liquid, and, in an applicator portion, a conduit extending from the reservoir to an outlet opening. The sachet further comprises an applicator pad that covers said opening. The applicator portion is folded and sealed onto the reservoir portion such that a sharp fold is present between the reservoir portion and the applicator portion. The fold blocks the conduit such that a liquid held in the reservoir is prevented from flowing into the conduit. Furthermore, the applicator portion comprises a grip tab between two tear lines. By pulling the tab, the applicator portion tears along the tear lines and part of the applicator portion can be unfolded to allow liquid to flow from the reservoir into the pad.

14 Claims, 1 Drawing Sheet

(56) References Cited

U.S. PATENT DOCUMENTS

2007/0045341 A1    3/2007  Bauer
2009/0241277 A1*  10/2009  Lam .......................... B08B 1/00
                                                        15/104.94
2016/0113377 A1*  4/2016  Moussion ........... A61M 35/003
                                                        401/132

* cited by examiner

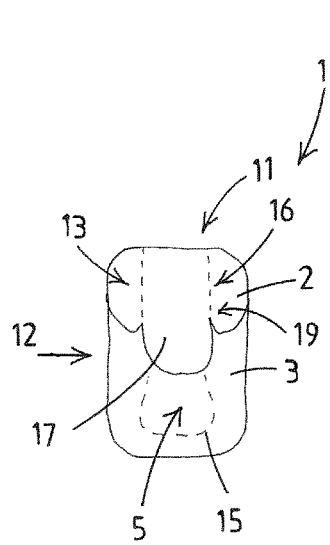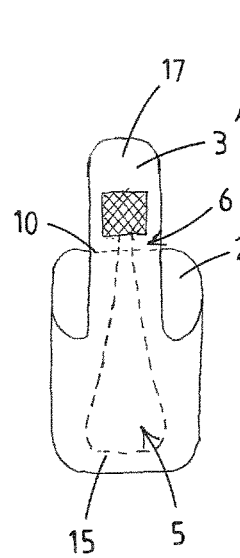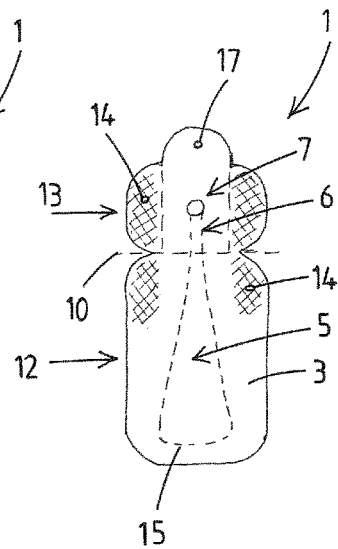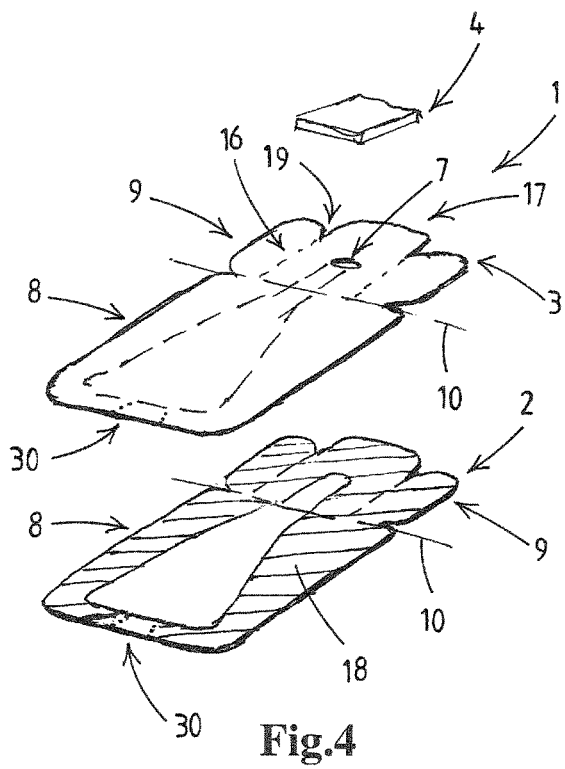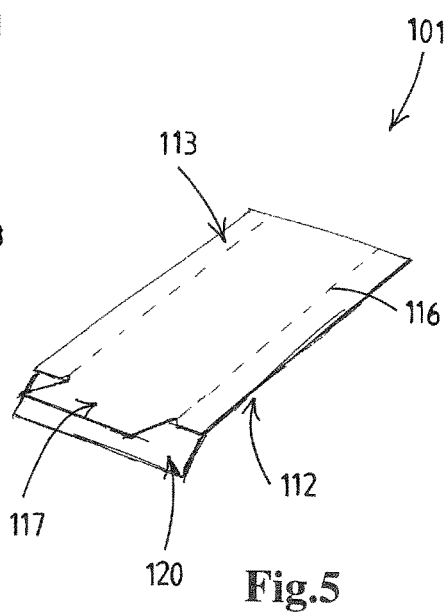

DISPOSABLE LIQUID APPLICATOR SACHET

FIELD AND BACKGROUND OF THE INVENTION

Known disposable liquid applicator sachets comprise a reservoir holding a liquid and an applicator pad for dispensing the liquid. The dispensing pad is used for controlled application of the liquid, for example on as a wipe. Typically, the liquid is held in a pouch, such as a sealed plastic bag. Prior to use the pouch is to be pierced or torn open to allow the liquid to flow onto the pad. Thus opening a pouch often requires great force and/or leads to uncontrolled movements while opening the pouch. Furthermore, combining pouch and applicator often leads to a relatively complicated product.

Especially with low cost disposable products such as a disposable liquid applicator sachet any improvement on use and/or simplification in production is an advantage.

It is an object of the invention to obviate the problems described hereinabove and in particular to provide an alternative disposable liquid applicator sachet, preferably an improved alternative disposable liquid applicator sachet. It is a further aspect of the invention to provide a disposable liquid applicator sachet that is easy to use and/or can be obtained at low cost.

SUMMARY OF THE INVENTION

According to the present invention, this object is achieved by providing a disposable liquid applicator sachet according to claim 1.

A disposable liquid applicator sachet comprises a top sheet, a base sheet and am applicator pad.

The base sheet and the top sheet both have a reservoir sheet portion and an applicator sheet portion. The top sheet is sealed onto said base sheet such that the reservoir sheet portions of said sheets define between them a reservoir for holding a liquid, and the applicator sheet portions of said sheets define between them a conduit, which conduit extends from the reservoir up to an outlet opening provided in the applicator sheet portion of the top sheet.

The applicator pad is attached to the applicator sheet portion of the top sheet, such that the applicator pad covers the outlet opening.

The sachet is folded with its applicator portion onto its reservoir portion and a sharp fold is present between the reservoir portion of the sachet and the applicator portion of the sachet. The sharp fold blocks the conduit to such an extent that a liquid held in the reservoir is prevented from flowing into the conduit.

The applicator portion of the sachet is sealed onto the reservoir portion of the sachet in sealing zones, which sealing zones are located on opposite sides of the conduit, and which sealing zones extend up to the fold.

The applicator portion of the sachet comprises a tear line on each side of the conduit, which tear lines are each located between the conduit and a sealing zone and which tear lines extend from an edge of the applicator portion up to the fold.

The applicator portion further comprises a grip tab for pulling the applicator portion of the sachet away from the reservoir portion of the sachet, which grip tab is provided between the two tear lines at a distance from the fold, such that by pulling the grip tab away from the reservoir portion of the sachet, the applicator portion tears along the tear lines and a part of the applicator portion of the sachet, the part comprising the conduit and the outlet opening, can be unfolded to allow a liquid held in the reservoir to flow into the conduit and out of the outlet opening into the applicator pad.

A liquid applicator sachet according to the invention comprises sheets and an applicator pad. The sheets are sealed together, for example by way of heat sealing, such that they provide a reservoir to contain a liquid prior to use. Thus, the reservoir is an integral part of the applicator. No additional components, such as a sealed plastic bag or pouch or other restraint means, are needed to hold the liquid prior to use.

Since the applicator and reservoir for holding liquid can be obtained by laminating sheets together, production costs can be kept low.

Furthermore, with the folded liquid applicator sachet, the applicator pad is shielded and thus substantially protected from contamination. By simply unfolding the disposable liquid applicator sachet, the applicator pad is exposed and simultaneously the conduit connecting the reservoir with the outlet opening is unblocked. Thus, any liquid held in the reservoir is allowed to flow via the conduit on the absorbent applicator pad, and the applicator is made ready for use. Thus, the applicator is simple to use.

The invention thus provides a simple disposable liquid applicator sachet which can be obtained at low cost.

A disposable liquid applicator sachet according to the invention is in particular suitable for dispensing small amounts of liquid, more in particular single use volumes. The sachet can for example be used for dispensing a single use volume of skin cream, sun screen, iodine or skin moisturiser.

Also, a disposable liquid applicator sachet is advantageous when applying a liquid to a vulnerable surface, since thin material the sachet is made of allows for good tactile feedback while applying the liquid on a surface. Furthermore, the configuration of the sachet allows for an embodiment in which, when the sachet is unfolded, the reservoir portion can be held between the thumb and base of the index and/or middle finger such that the reservoir portion with the sachet is located at the tip or tips of the index and/or middle finger. Thus, while applying the liquid the applicator part, and thus the applicator, can be manipulated using the index and/or middle finger, which allows for applying acute and price manipulation and pressure. In a further embodiment, the sachet is dimensioned such that its width matches the combined width of an average middle and index finger, to further facilitate holding and manipulating the sachet with these fingers.

In an embodiment the sachet is folded with its applicator portion onto its reservoir portion such that the applicator pad faces the reservoir portion of the sachet. Thus the applicator pad is shield from the environment prior to use, which protects the applicator part and reduces the chance that the applicator pad gets contaminated.

In an embodiment along an edge of the reservoir portion of the sachet the top sheet is not sealed onto the base sheet such that a filling opening is provided between the top sheet and the base sheet, which filling opening provides access to the reservoir for filling said reservoir with a liquid. Thus, the sachet can be manufactured in a first location and filled in a second location. After filling only a simple sealing step remains to seal the reservoir.

In a further embodiment, the filling opening is provided in the edge of the reservoir portion of the sachet opposite the conduit, such that the reservoir is located between the conduit and the filling opening. This allows for a simple filling operation. In particular when the sachet is provided with an elongate reservoir, for example a triangular shaped reservoir that converges towards the conduit, providing the filling opening opposite the conduit allows facilitates positioning a filling needle in the reservoir, and reduces the chance of the needle piercing the sachet.

The unfilled sachet is considered an intermediate product, which, by filling and sealing the reservoir can be turned into the final product.

In an embodiment, the reservoir is substantially triangular shaped such that it converges towards the conduit. The triangular, converging shape of the reservoir facilitates forcing a liquid into the conduit, by pinching the reservoir portion in a direction towards the conduit. An elongate reservoir facilitates applying the liquid to the applicator pad is subsequent steps, thus providing multiple dosses of liquid to the pad.

In an embodiment, the applicator portion only covers a part of the reservoir portion, and the uncovered part of the reservoir portion forms a grip for holding the reservoir portion when pulling the applicator portion away from the reservoir portion. Thus, reservoir portion can function as a grip, which allows for a compact configuration of the sachet since not additional taps are needed.

In an embodiment, the reservoir portion comprises a grip tab adjacent the reservoir for holding the reservoir portion when pulling the applicator portion away from the reservoir portion. The grip tab may be provided with for example apertures or ribs to enhance the grip properties and provide an anti-slip surface.

In an embodiment, the base sheet and/or the top sheet are a laminate of multiple layers of sheet material sealed together. By combining sheets of different materials and/or having different properties, the base sheet and the top sheet can be provided with specific properties. For example, the sheets can be a laminate of a barrier sheet made of a material particularly suitable for holding a liquid to be applied, a carrier sheet of a relatively stiff, non-resilient and foldable material, and a cover layer of a material upon which text ad figures can be printed.

In an embodiment, the edge of the applicator portion is provided with V-shaped cut outs at the ends of the tear lines opposite the fold, to instigate tearing of the applicator portion at the tear lines when the applicator portion is pulled away from the reservoir portion. These V-shaped cut outs are preferably provided were the tab portion meets the sealing area, at the beginning of a tear lines.

In an embodiment, the base sheet and the top sheet are made of a plastic sheet material, for example a Polypropylene material. In an embodiment, the base and top sheet have a thickness in the range of 30-200 micron.

In an embodiment, a top sheet of the sachet according to the invention is sealed to the base sheet over more than 30 percent of its surface area, preferably over more than 50 percent of its surface area, for example over 70 percent of its surface area. Thus, the applicator has a compact, substantially flat, sheet like appearance and maintains this configuration during use.

In an embodiment, the top sheet is provided with user information that indicates where and how to press on the reservoir such that, when in the sachet is torn open, the reservoir should be pressed to distribute a liquid from the reservoir to the applicator pad.

The applicator pad is made of an absorbent material, for example a woven or now woven cotton or molleton material. The pad is for example glued onto the top sheet of the sachet It is noted that in use, the reservoir portion is used as a grip for handling the sachet while applying the liquid with the applicator pad.

The invention furthermore provides a method according for obtaining a disposable liquid applicator sachet according to the invention. The method comprises the steps:
provinding the base sheet and the top sheet, the latter having an outlet opening;
sealing the top sheet upon the base sheet such that they define between them a reservoir and a conduit, while leaving a filling opening between the top sheet and the base sheet for filling the reservoir;
preferably weakening the applicator portion along the tear lines, for example by providing apertures and/or a surface cut along the tear lines;
applying the applicator pad onto the top sheet over the outlet opening; and
folding the applicator portion of the sachet onto the reservoir portion of the sachet
sealing applicator portion to reservoir portion.

It is noted that in practice, the order of steps may differ.

To turn the sachet form an intermediate product into a final product, the method furthermore comprises the steps:
filling the reservoir with a liquid via the filling opening: and
laminating the top sheet onto the base sheet at the filling opening to seal the filling opening.

It is noted that in the context of this publication, a liquid can also be a paste or similar suitable for impregnating the applicator pad, for example a sun screen, shoe polish, wax, skin cream, etc.

Advantageous embodiments of the disposable liquid applicator sachet according to the invention and the method according to the invention are disclosed in the subclaims and in the description, in which the invention is further illustrated and elucidated on the basis of a number of exemplary embodiments, of which some are shown in the schematic drawing.

BRIEF DESCRIPTION OF THE DRAWINGS

In the drawings:
FIG. 1 shows a first exemplary embodiment of a sachet according to the invention;
FIG. 2 shows the sachet of FIG. 1 torn open and ready for use;
FIG. 3 shows the sachet of FIG. 1 in an unfolded state;
FIG. 4 shows an exploded view of the sachet of FIG. 1 in an unfolded state; and
FIG. 5 shows as second exemplary embodiment of a sachet according to the invention.

DETAILED DESCRIPTION

First, the invention will be further elucidated on the basis of the exemplary embodiment of a disposable liquid applicator sachet according to the invention as shown in FIGS. 1-3. Thereafter, some particular alternative embodiments will be described.

FIG. 1 shows the disposable liquid applicator sachet in its folded state, and FIG. 2 shows the sachet in its opened state, in which it ready for use. FIG. 3 shows the sachet during production, in its unfolded state, and FIG. 4 shows an exploded view of the sachet in its unfolded state.

The sachet 1 shown in FIGS. 1-3 comprises two sheets, a base sheet 2 a top sheet 3 and an applicator pad 4. The base sheet 2 and the top sheet 3 are sealed onto each other such that the form between them a reservoir 5 and a conduit 6. The reservoir and conduit are indicating with a hatched line 15. The conduit 6 connects the reservoir 5 with an outlet opening 7 provided in the top sheet 3.

As is indicated in the exploded view, both the base sheet and the top sheet having a reservoir sheet portion 8 and an applicator sheet portion 9. During production, the top sheet 3 is sealed onto the base sheet 2 such that the reservoir sheet portions 8 of the sheets 2,3 define between them the reservoir 5 for holding a liquid, and the applicator sheet portions 9 of the sheets define between them the conduit 6. The conduit 6 ends beneath the outlet opening 7 provided in the top sheet 3, and thus below the applicator pad 4 that is attached to the applicator sheet portion 9 of the top sheet 3 such that it covers the outlet opening.

By selectively laminating the two sheets 2,3 onto each other, the layout of reservoir 6 and conduit 6 can be defined. In the exemplary embodiment shown, the sheets 2,3 both have a substantially rectangular shape. The sheets 2,3 are sealed onto each other over a substantial surface area, i.e. at least 50 percent of their surface area. The sealing areas are indicated with a hatched pattern 18.

On both the top sheet 3 and the base sheet 2 is also indicated, with dotted lines, the filling opening 30 via which the reservoir can be filled. At the filling opening the base sheet and top sheet are sealed together after the top sheet has been sealed upon the base sheet to define the reservoir and conduit, the applicator portion has been sealed upon reservoir portion to block the conduit, and the reservoir has been filled via said filling opening. It is observed that the filling opening can also be provided at other locations along the border of the reservoir.

These sealed areas of the sheets, at which the top sheet has been applied to the base sheet, provide the sachet with rigidity and a secure its substantially flat shape prior to and during use.

In the embodiment shown, the reservoir has a substantially triangular layout, such that it converges towards the conduit. This shape is beneficial for pushing liquid form the reservoir into the conduit. Alternative shapes are also possible, for example a more rectangular shaped reservoir or a reservoir with an oval or circular lay out.

Also, for example, a sachet according to the invention can be provided with multiple parallel conduits that run between the reservoir and the outlet opening.

Also, instead of a single outlet opening as shown, a sachet according to the invention can be provided with multiple outlet openings, which can each be fed by the same conduit or can each be provided with their own conduit. Thus, the applicator pad can be more evenly impregnated, i.e. impregnated over a large surface area instead of for example only in the centre of the applicator pad.

Also, a sachet according to the invention can be provided with two or more separate reservoirs can be provided adjacent each other, each with one or more conduits connecting the reservoir with one or more outlet openings.

In FIGS. 3 and 4 a fold line 11 is depicted, which fold line separates the reservoir portion 12 of 10 the sachet 1, the reservoir portion comprising the reservoir sheet portions 8 and the reservoir 5 defined thereby, from the applicator portion 13 of the sachet, the applicator portion comprising the applicator sheet portions 9 and the conduit 6 defined thereby.

To obtain the folded state, in which the sachet 1 is depicted in FIG. 1, the sealed sheets are folded along the fold line 10. Thus, the applicator portion 13 of the sachet is folded onto the reservoir portion 12 of the sachet 1, such that the applicator pad 4 faces the reservoir portion of the sachet.

The sachet 1 is folded such that a sharp fold 11 is present between the reservoir portion 12 of the sachet and the applicator portion 13 of the sachet. The sharp fold 11 blocks the conduit 6 to such an extent that a liquid held in the reservoir 4 is prevented from flowing into the conduit 6. It is observed that due to the fold being a sharp fold, the sachet is folded over an angle of 360 degrees such that adjacent the fold the surface of the applicator part facing the reservoir part is located adjacent the surface of the reservoir part.

To maintain the sharp fold 11, and keep the conduit blocked, until the sachet is to be used to apply liquid, the applicator portion 13 of the sachet 1 is sealed onto the reservoir portion 12 of the sachet in sealing zones 14, which sealing zones are located on opposite sides of the conduit 6, and which sealing zones extend up to the fold. The sealing zones 14 are indicated with a cross hatched pattern in FIG. 3.

It is observed that in the preferred embodiment shown, the sealing zones 14 run up to the fold 11 such that they provide for a sharp fold to be present between the reservoir portion 12 and the applicator portion 13 of the sachet 1.

The applicator portion 13 of the sachet is folded onto the reservoir portion 12 of the sachet such that the applicator pad 4 is facing the reservoir portion. Thus, the applicator pad is shielded from the environment, and the risk of contamination of the pad prior to its use for applying liquid is reduced.

According to the invention, the applicator portion 13 of the sachet comprises a tear line 16 on each side of the conduit 6.

These tear lines 16 are each located between the conduit 6 and a sealing zone 14, in which the applicator portion 13 is sealed to the reservoir portion to secure the sachet in its folded position with a sharp fold between the applicator portion and the reservoir portion.

Furthermore, according to the invention, the tear lines 16 extend from an edge of the applicator portion 13 up to the fold 11. Thus, the tear lines 16 allow part of the applicator portion 13, the part comprising the conduit 6, to be unfolded by tearing the applicator portion along the tear lines, and thus remove the sharp fold 11 to unblock the conduit, as will be explained in more detail below.

According to the invention, the applicator portion 13 of the sachet 1 comprises a grip tab 17 for pulling the applicator portion of the sachet away from the reservoir portion 12 of the sachet. The grip tab 17 is provided between the two tear lines 16 at a distance from the fold 11. By pulling the grip tab 17 away from the reservoir portion 12 of the sachet, the applicator portion 13 tears along the tear lines 16 and the part of the applicator portion comprising the conduit 6 and the outlet opening 7 is unfolded. By unfolding this part of the applicator portion, the fold 11 that blocks the conduit 6 is removed. A liquid held in the reservoir 5 can thus flow into the conduit 6 and out of the outlet opening 7 into the applicator pad 4.

In the embodiment shown, the tear lines are defined by a series of apertures provided in the base sheet and the top sheet. The apertures can be applied to the sheets prior to laminating them onto each other, for example while cutting the sheets out of a larger piece of sheet material. Alternatively, the apertures can be provided after the base sheet and the top sheet are sealed onto each other, such that both sheets are perforated in a single step. Alternative techniques can be applied to provide the sheets with tear lines, for example by partially cutting the sheets or providing a groove in the surface of the sheets. Other suitable techniques for applying a tear line known in the prior art can also be used.

In the exploded view of the exemplary embodiment 1 shown in FIG. 4, the top sheet 3 and the base sheet 2 are separate, pre-cut sheets, which sheets are to be placed upon each other prior to laminating them together. In an alternative embodiment, the sheets can be cut into shape after being sealed together. Thus, for example, two strips of sheet material can be positioned on top of each other and subsequently be sealed together and cut to form a string of sachets, which sachets are only separated after being filled with a liquid and sealed.

Furthermore, instead of combing two separate sheets, a single sheet can be folded to obtain a top sheet positioned onto a base sheet.

In the embodiment of the sachet 1 shown, the base sheet 3 and the top sheet 3 are each laminates comprising multiple layers of different materials. The sheets each comprise a barrier sheet, made of a material particularly suitable for holding a liquid to be applied, a carrier sheet, of a relatively stiff, non-resilient and foldable material, and a cover layer, of a material upon which text ad figures can be printed.

By combining sheets materials into a single sheet, the properties of the base and top sheet can be configured to fit a particular use and/or liquid. For example, the sheets can be provided with a rough top layer to provide users with a better grip when pulling the sachet open, or with a barrier material that prevents light from reaching the liquid in the reservoir, for example to lengthen the shelf life of the product.

In an exemplary embodiment of a production process for obtaining a sachet according to the invention, first an intermediate product is created. With the intermediate product the base sheet and top sheet are already sealed together and the applicator portion is already sealed upon the reservoir portion of the sachet. However, the top sheet and the base sheet are not yet sealed together along the entire edge of the reservoir portion to provide a filling opening for the reservoir, preferably provide a filling opening along the bottom of the reservoir, i.e. opposite the conduit. Since the applicator portion has already been secured in its position upon the reservoir portion, the conduit is blocked and the reservoir of the intermediate product can be filled, for example by inserting a filling needle in the reservoir via the above mentioned filling opening, without the risk of the liquid flowing into the conduit and out of the outlet. After the reservoir has been filled with a liquid, the top sheet and the base sheet are also sealed together at the filling opening, for example by way of heat sealing, thus the reservoir is closed and the final product is ready for distribution.

As already mentioned, according to the invention, the applicator portion 13 of the sachet 1 comprises a grip tab 17 for pulling the applicator portion of the sachet away from the reservoir portion 12 of the sachet. In the embodiment shown, the applicator portion only partially covers the reservoir portion of the sachet. Thus, the uncovered part of the reservoir portion can be used to hold the sachet, more in particular the reservoir portion of the sachet, when part of the applicator portion is torn away from the reservoir portion by pulling the grip tab.

FIG. 5 shows an alternative sachet 101 according to the invention, of which the applicator portion 113 covers substantially the entire reservoir portion 112. The reservoir portion is provided with a grip tab 120, i.e. a part of the reservoir portion in which the top sheet is fully sealed onto the base sheet, and no reservoir is present between the sheets. The grip tab 120 of the reservoir portion is provided to hold the sachet 101, more in particular the reservoir portion 112 of the sachet, when pulling the grip tab 117 provided at the applicator portion 113 away from the reservoir portion to tear the applicator portion 113 along the tear lines 116. Thus, according to the invention, the sachet 101 can be partially unfolded, to expose the applicator pad and simultaneously unblock the conduit connecting the reservoir with the outlet opening provided below the pad.

By pulling the grip tab 17 away from the reservoir portion 12 of the sachet, the applicator portion 13 tears along the tear lines 16 and the part of the applicator portion comprising the conduit 6 and the outlet opening 7 is unfolded. By unfolding this part of the applicator portion, the fold 11 that blocks the conduit 6 is removed. A liquid held in the reservoir 5 can thus flow into the conduit 6 and out of the outlet opening 7 into the applicator pad 4. To force the liquid into and out of the conduit, a user can pinch or squeeze the reservoir between his fingers, preferably between thumb and index finger.

Once the liquid has impregnated the porous applicator pad, the liquid can be applied, for example on the skin of a person for cleaning said skin or on a wound for decontamination purposes. The particular application of the sachet depends on the liquid held in the reservoir and the intended use.

When applying the liquid, the sachet can be held by its reservoir portion and/or its application portion. The sachet according to eh invention is particularly useful for applying It is noted that the substantially flat configuration of a sachet according to the invention allows for easy storage, a user can for example carry along a sachet in its wallet. Also, the sachet allows can be included in a magazine, for example for the distribution of samples of a product.

Furthermore, the flat surfaces provide an optimal surface for providing the sachet with texts and pictures, such as trademarks, relevant product information, etc. With more voluminous sachets, for example pillow shaped sachets, convex surfaces may render text illegible Wherein the front sheet is provided with user information that indicates where and how to press on the reservoir such that, when in the unfolded position, the reservoir should be pressed to distribute a liquid from the reservoir to the applicator pad In the exemplary embodiment shown, the tear lines 16 are defined by a series of apertures provided in the base sheet and the top sheet. The apertures can be applied to the sheets prior to laminating them onto each other, for example while cutting the sheets out of a larger piece of sheet material. Alternatively, the apertures can be provided after the base sheet and the top sheet are sealed onto each other, such that both sheets are perforated in a single step. Alternative techniques can be applied to provide the sheets with tear lines, for example by partially cutting the sheets or providing a groove in the surface of the sheets. Other suitable techniques for applying a tear line known in the prior art can also be used.

In the exemplary embodiment shown, the edge of the applicator portion 13 is provided with V-shaped cut outs 19 at the ends of the tear lines 16 opposite the fold 11, to instigate tearing of the applicator portion at the tear lines when the applicator portion is pulled away from the reservoir portion. These V-shaped cut outs are preferably provided were the tab portion meets the sealing area, at the beginning of a tear lines.

It is noted that the intermediate product can roughly look like the final product, for example as depicted in FIG. 1, with the differences that the reservoir has not yet been filed and a filling opening is present. It is furthermore noted that he filling opening can be provided at the bottom of the reservoir, but also along the sides of the reservoir.

In the context of this publication, a tear line is to be understood as the line along which the applicator portion will tear when, after the applicator portion has been sealed to the reservoir portion, the applicator portion is pulled away from the reservoir portion. Preferably, the applicator portion is weakened along the tear line to instigate and/or define the tear line. For example, the surface of the applicator portion can be partially cut, apertures or perforations can be provided along the tear line, V/shaped cut outs can be provided at the edge of the applicator portion, etc.

Other variations to the disclosed embodiments can be understood and effected by those skilled in the art in practicing the claimed invention, from study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope. The invention is by no means limited to the exemplary embodiment described herein above, but comprises various modifications hereto, in so far as they fall within the scope of the following claims.

REFERENCE SIGNS 1 first exemplary embodiment
2 base sheet
3 top sheet
4 applicator pad
5 reservoir
6 conduit
7 outlet opening in top sheet
8 reservoir sheet portion
9 applicator sheet portion
10 fold line
11 sharp fold
12 reservoir portion sachet
13 applicator portion sachet
14 sealing zones
15 hatched line that indicates reservoir and conduit
16 tear line
17 grip tab
18 hatched pattern sealing area's
19 V-shaped cut-outs

The invention claimed is:

1. A disposable liquid applicator sachet, comprising:
a base sheet and a top sheet, each of the base sheet and the top sheet having a reservoir sheet portion and an applicator sheet portion, and said top sheet being sealed onto said base sheet such that the reservoir sheet portions of said base sheet and said top sheet define therebetween a reservoir for holding a liquid, and the applicator sheet portions of said base sheet and said top sheet define therebetween a conduit, which conduit extends from the reservoir up to an outlet opening provided in the applicator sheet portion of the top sheet; and
an applicator pad, which applicator pad is attached to the applicator sheet portion of the top sheet, such that the applicator pad covers the outlet opening,
wherein the disposable liquid applicator sachet is folded with an applicator portion thereof onto a reservoir portion thereof, and wherein a sharp fold is present between the reservoir portion of the disposable liquid applicator sachet and the applicator portion of the disposable liquid applicator sachet, which sharp fold blocks the conduit to such an extent that the liquid held in the reservoir is prevented from flowing into the conduit,
wherein the applicator portion of the disposable liquid applicator sachet is sealed onto the reservoir portion of the disposable liquid applicator sachet in sealing zones, which sealing zones are located on opposite sides of the conduit, and which sealing zones extend up to the fold,
wherein the applicator portion of the disposable liquid applicator sachet comprises a tear line on each side of the conduit, which tear lines are each located between the conduit and a sealing zone and which tear lines extend from an edge of the applicator portion up to the sharp fold, and
wherein the applicator portion of the disposable liquid applicator sachet comprises a grip tab for pulling the applicator portion of the disposable liquid applicator sachet away from the reservoir portion of the disposable liquid applicator sachet, which grip tab is provided between the two tear lines at a distance from the fold, such that by pulling the grip tab away from the reservoir portion of the disposable liquid applicator sachet, the applicator portion tears along the tear lines and a part of the applicator portion of the disposable liquid applicator sachet, the part comprising the conduit and the outlet opening, can be unfolded to allow the liquid held in the reservoir to flow into the conduit and out of the outlet opening into the applicator pad.

2. The disposable liquid applicator sachet according to claim 1, wherein the disposable liquid applicator sachet is folded with the applicator portion thereof onto the reservoir portion thereof such that the applicator pad faces the reservoir portion of the disposable liquid applicator sachet.

3. The disposable liquid applicator sachet according to claim 1, wherein, along an edge of the reservoir portion of the disposable liquid applicator sachet, the top sheet is not sealed onto the base sheet such that a filling opening is provided between the top sheet and the base sheet, which filling opening provides access to the reservoir for filling said reservoir with the liquid.

4. The disposable liquid applicator sachet according to claim 3, wherein the filling opening is provided in the edge of the reservoir portion of the disposable liquid applicator sachet opposite the conduit, such that the reservoir is located between the conduit and the filling opening.

5. The disposable liquid applicator sachet according to claim 1, wherein the reservoir is filled with the liquid.

6. The disposable liquid applicator sachet according to claim 1, wherein the reservoir is substantially triangular shaped such that the reservoir converges towards the conduit.

7. The disposable liquid applicator sachet according to claim 1, wherein the applicator portion only covers a part of the reservoir portion, and the uncovered part of the reservoir portion forms a grip for holding the reservoir portion when pulling the applicator portion away from the reservoir portion.

8. The disposable liquid applicator sachet according to claim 1, wherein the reservoir portion comprises a grip tab adjacent the reservoir for holding the reservoir portion when pulling the applicator portion away from the reservoir portion.

9. The disposable liquid applicator sachet according to claim 1, wherein the base sheet and/or the top sheet are a laminate of multiple layers of sheet material sealed together.

10. The disposable liquid applicator sachet according to claim 1, wherein the edge of the applicator portion is provided with V-shaped cut outs at ends of the tear lines opposite the fold, to instigate tearing of the applicator portion at the tear lines when the applicator portion is pulled away from the reservoir portion.

11. A method for providing the disposable liquid applicator sachet according to claim 1, comprising the steps:
providing the base sheet and the top sheet, the top sheet having an outlet opening;
sealing the top sheet upon the base sheet such that the top sheet and the base sheet define therebetween a reservoir and a conduit, while leaving a filling opening between the top sheet and the base sheet for filling the reservoir;
weakening the applicator portion along the tear lines;
applying the applicator pad onto the top sheet over the outlet opening;
folding the applicator portion of the disposable liquid applicator sachet onto the reservoir portion of the disposable liquid applicator sachet to seal the applicator portion to the reservoir portion.

12. The method according to claim 11, further comprising the steps:
filling the reservoir with the liquid via the filling opening; and
laminating the top sheet onto the base sheet at the filling opening to seal the filling opening.

13. The disposable liquid applicator sachet according to claim 2, wherein, along an edge of the reservoir portion of the disposable liquid applicator sachet, the top sheet is not sealed onto the base sheet such that a filling opening is provided between the top sheet and the base sheet, which filling opening provides access to the reservoir for filling said reservoir with the liquid.

14. The disposable liquid applicator sachet according to claim 2, wherein the reservoir is filled with the liquid.

* * * * *